(12) United States Patent
Montalvo et al.

(10) Patent No.: US 7,494,479 B2
(45) Date of Patent: Feb. 24, 2009

(54) SYRINGE WITH RETRACTABLE NEEDLE ASSEMBLY

(75) Inventors: Rudy Montalvo, Woodland Hills, CA (US); Raymond P. Feith, Chino Hills, CA (US); Susan McConnell-Montalvo, Woodland Hills, CA (US); April Marano-Ford, Manhattan Beach, CA (US)

(73) Assignee: Medsolve Technologies, Inc., Manhattan Beach, CA (US)

( * ) Notice: Subject to any disclaimer, the term of this patent is extended or adjusted under 35 U.S.C. 154(b) by 961 days.

(21) Appl. No.: 10/247,781

(22) Filed: Sep. 16, 2002

(65) Prior Publication Data

US 2004/0054324 A1    Mar. 18, 2004

(51) Int. Cl.
*A61M 5/00*    (2006.01)

(52) U.S. Cl. ..................................... 604/110

(58) Field of Classification Search ............... 604/110, 604/195, 187, 192–198, 220, 218; 128/919
See application file for complete search history.

(56) References Cited

U.S. PATENT DOCUMENTS

| | | | | |
|---|---|---|---|---|
| 4,863,247 A | | 9/1989 | Lasher et al. ............... | 350/401 |
| 5,112,316 A | * | 5/1992 | Venturini .................... | 604/198 |
| 5,211,628 A | * | 5/1993 | Marshall .................... | 604/110 |
| 5,267,961 A | * | 12/1993 | Shaw ......................... | 604/110 |
| 5,458,576 A | * | 10/1995 | Haber et al. ................ | 604/110 |
| 5,484,421 A | | 1/1996 | Smocer ....................... | 604/195 |
| 5,693,023 A | | 12/1997 | Adams ........................ | 604/195 |
| 5,782,804 A | | 7/1998 | McMahon ................... | 604/110 |

(Continued)

FOREIGN PATENT DOCUMENTS

FR    2 727 021 A    5/1996

(Continued)

OTHER PUBLICATIONS

U.S. Appl. No. 10/190,441, filed Jul. 2, 2002 to Woodard et al.

(Continued)

*Primary Examiner*—Kevin C Sirmons
*Assistant Examiner*—Elizabeth R MacNeill
(74) *Attorney, Agent, or Firm*—Connolly Bove Lodge & Hutz LLP (57) ABSTRACT

A hypodermic syringe employing a plunger slidably disposed within a barrel. The plunger has a mounting hole extending through the seal end thereof to receive a mandrel. The mandrel has a flexible flange to be releasably engaged with the plunger. A spring element withdraws the mandrel into a cavity within the plunger upon full extension of the plunger within the barrel. The barrel includes a hub retainer at the forward end thereof and a needle hub retained therein the mandrel includes barbed tines with surfaces having axes of the conical surfaces that are displaced from one another such that movement of the tines toward one another also brings the axes closer. A catch associated with the back end of the spring element coupled with the mandrel at the other end cooperates with shoulders on smooth surfaces within the cavities to retain tension within the bungee. The hub retainer and the needle hub cooperate to insure that the needle hub is constrained to limited motion such that the mandrel will fully engage the needle hub.

3 Claims, 8 Drawing Sheets

U.S. PATENT DOCUMENTS

| | | | |
|---|---|---|---|
| 5,961,491 A | 10/1999 | McGary et al. | 604/110 |
| 5,993,417 A * | 11/1999 | Yerfino et al. | 604/110 |
| 6,017,325 A * | 1/2000 | Yerfino et al. | 604/110 |
| 6,050,977 A | 4/2000 | Adams | 604/195 |
| 6,409,701 B1 | 6/2002 | Cohn et al. | 604/110 |
| 6,517,516 B1 | 2/2003 | Caizza | 604/110 |
| 6,676,641 B2 | 1/2004 | Woodard, Jr. et al. | 604/187 |
| 2003/0023205 A1 * | 1/2003 | Botich et al. | 604/110 |

FOREIGN PATENT DOCUMENTS

| | | |
|---|---|---|
| WO | WO 91/03269 A | 3/1991 |
| WO | WO 01/41830 A | 6/2001 |
| WO | WO 01/41843 | 6/2001 |
| WO | WO 02/066097 | 8/2002 |

OTHER PUBLICATIONS

U.S. Appl. No. 10/450,573, filed Jan. 7, 2002 to Field et al.
U.S. Appl. No. 10/345,901, filed Jan. 16, 2003 to Campbell et al.

* cited by examiner

SYRINGE WITH RETRACTABLE NEEDLE ASSEMBLY

BACKGROUND OF THE INVENTION

The field of the present invention is syringes and, more particularly, syringes offering protection against accidental sharps injury.

Accidental sharps injuries, in this context needle sticks, have long been recognized as potentially dangerous to health care workers. More recently, the transmission of serious and potentially fatal infections from such sharps injuries have created greater concern. Legislation has been contemplated in a number of States and before the Occupation Safety and Health Administration which would require safe needle technology.

A number of approaches have been undertaken to provide protection against such sharps injuries. International Publication WO 01/41843A1 discloses a syringe with a retractable needle which includes a plunger having a cavity extending longitudinally therein. A spring element is located in the cavity and is fixed to a mandrel extending into the syringe barrel from the mandrel which attaches to and retracts a needle into the barrel. The other end of the spring element is associated with a catch which causes the spring element to be placed in tension as the plunger is advanced within the barrel. A retention assembly associated with the end of the plunger receives and secures the catch to retain the spring element in tension. Advancement of the plunger to the end of its stroke results in the capture of the needle assembly by the mandrel and the release of the mandrel from the seal end of the plunger, resulting in retraction.

A further refinement of the foregoing design is disclosed in International Publication WO 01/41830A2. Improvements incorporated into this latter device include resilient dogs retaining the needle assembly in the forward end of the barrel. A driver surface is provided on the plunger to move the dogs from engagement for retraction of the needle assembly. Further, teeth are provided along either side of the cavity through the plunger to provide a range of engagements for the catch on the back end of the spring element. The disclosures of the foregoing patent publications are incorporated herein by reference.

SUMMARY OF THE INVENTION

The present invention is directed to a hypodermic syringe including a barrel with a plunger slidably disposed therein. The plunger has a cavity extending longitudinally. A hole extends through the seal end of the plunger and receives a mandrel. A spring element within the cavity is fixed to the mandrel at one end and fixable relative to the plunger in a tensioned state at the other end. A needle hub is releasably mounted in a hub retainer at one end of the barrel. A number of specific features are provided to enhance syringe operation.

In a first separate aspect of the present invention, the mandrel positioned within the hole includes an annular flange which is flexible longitudinally of the plunger and engages one or more detents extending into the hole. This flexible flange provides a more uniform release without the need for very close tolerances and flexure of less resilient materials. The detent or detents may each provide an engagement surface which is at an acute angle to the longitudinal direction of the plunger to further enhance the uniformity of mandrel release.

In a second separate aspect of the present invention, the mandrel is provided with tines extending longitudinally of the plunger. These tines have a spaced therebetween and each has a barb with a conical surface facing outwardly. The axes of the conical barb surfaces are offset from one another such that they approach one another as the resilient tines are bent toward one another. The arrangement of the barbs is such that, as the barbs move, corresponding elements on the barb surfaces move toward defining a circle. This motion takes place as the tines are forced into an engagement hole on the needle hub. In this way, the center of the barb surfaces define the resistance to insertion within the engagement hole, insuring a more predictable and uniform resistance.

In a third separate aspect of the present invention, the barrel includes dogs which retain the needle hub at one end thereof. The barrel also includes a shoulder normal to the longitudinal direction of the barrel facing into the barrel. The needle hub includes a shoulder also normal to the longitudinal direction of the barrel which faces the barrel shoulder. The dogs and the shoulders define two positions, one with the needle hub against the dogs and one with the shoulders engaged. These positions are displaced from one another. The normal aspect of the shoulders provides a fixed position upon engagement of the shoulders advantageous for engagement and retraction of the needle hub by the mandrel. The displacement between positions aids in the assurance of the release of the needle hub by the dogs. It is also possible that an O-ring seal between the needle hub and the barrel is able to bias the hub toward the first position to give stable placement for injection. The location of the shoulders may be advantageously selected along the length of the needle hub.

In a fourth separate aspect of the present invention, the spring element includes a catch which is slidably mounted within the cavity of the plunger. The catch includes elements which are engageable with the barrel as the plunger moves further into the barrel. Additional elements engage shoulders defined within the plunger cavity. There are two opposed smooth walls in the cavity with one shoulder only in each wall. This enables placement of the shoulders to retain the catch such that resistance is not encountered from multiple engaging elements and yet the plunger need not be fully extended within the barrel for engagement.

Accordingly, it is an object of the present invention to provide an improved safety syringe with a retractable needle. Other and further objects and advantages will appear hereinafter.

DETAILED DESCRIPTION OF THE PREFERRED EMBODIMENTS

Figures 1, 2:
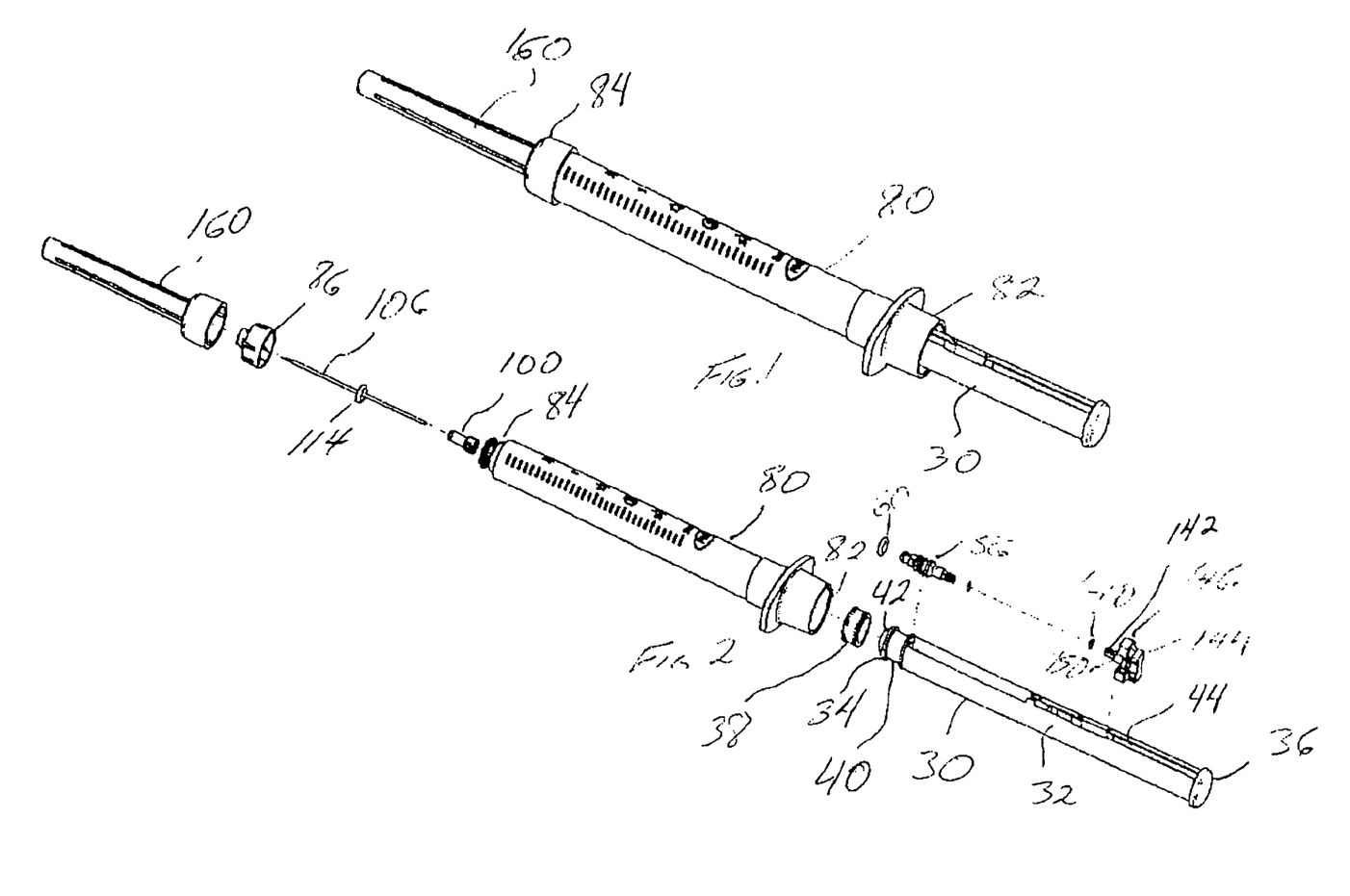
FIG. 1 is perspective view of a retractable hypodermic syringe.
FIG. 2 is an exploded assembly view in perspective of the device of FIG. 1.
Figure 3:
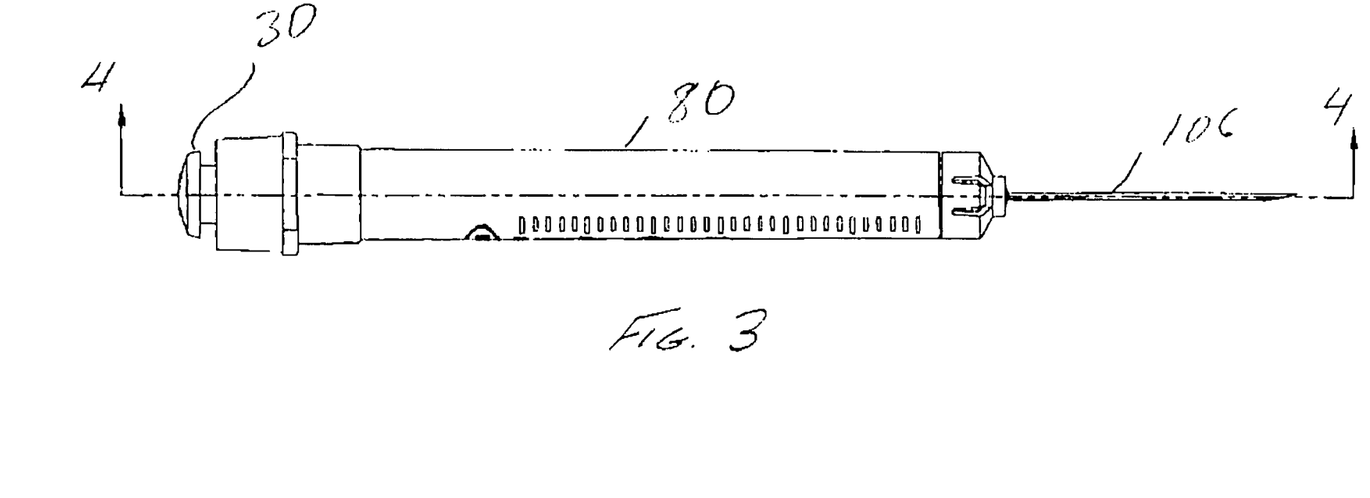
FIG. 3 is a side view of the device of FIG. 1.

Turning in detail to the drawings, FIG. 1 illustrates a syringe with a retractable needle. This view illustrates the device as shipped. FIG. 2 illustrates the same device in an exploded assembly view as including a barrel 80, a plunger assembly 30, a protective needle cap 160 and a needle hub 100 with an associated needle 106.

Figure 11:
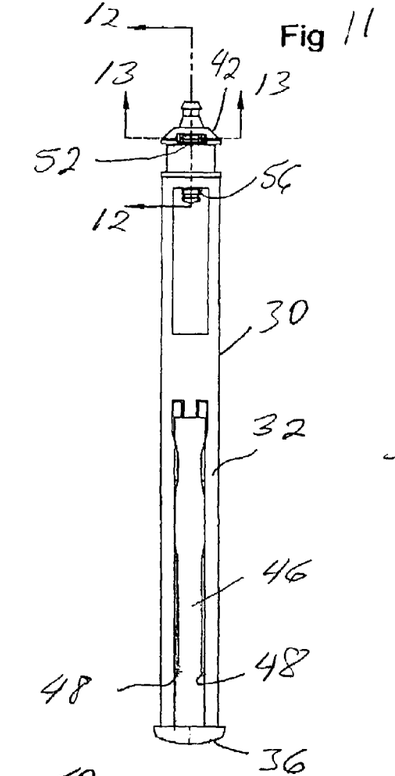
FIG. 11 is a front view of a plunger.

The plunger assembly is illustrated in various positions within the barrel 80 in FIGS. 4, 5, 6 and 7. Further, the plunger assembly is shown by itself in FIG. 11. The plunger assembly 30 includes a molded body 32 having a seal end 34 and an outer end 36. The outer end 36 defines a thumb button for actuation of the syringe while the seal end 34 acts as a piston with a ring seal 38 extending about a waist 40. A substantially conical forward surface defines a driver surface 42 which will be described later as interacting with the forward end of the barrel.

A cavity 44 lies between the seal end 34 and the outer end 36. This cavity is shown to be open on two sides and defined by two smooth surfaces 46 which are opposed and extend substantially the length of the cavity 44. Each of the smooth surfaces 46 has one shoulder 48. The shoulders 48 in the two surfaces face the outer end 36. These two shoulders 48 are aligned with one another to receive a catch as will be described below. The smooth surfaces 46 are curved near the middle of the body 32 to constrict the width of the cavity. This may be employed to arrest the motion of the needle as it is being retracted into the syringe as will be discussed below.

Figure 12:
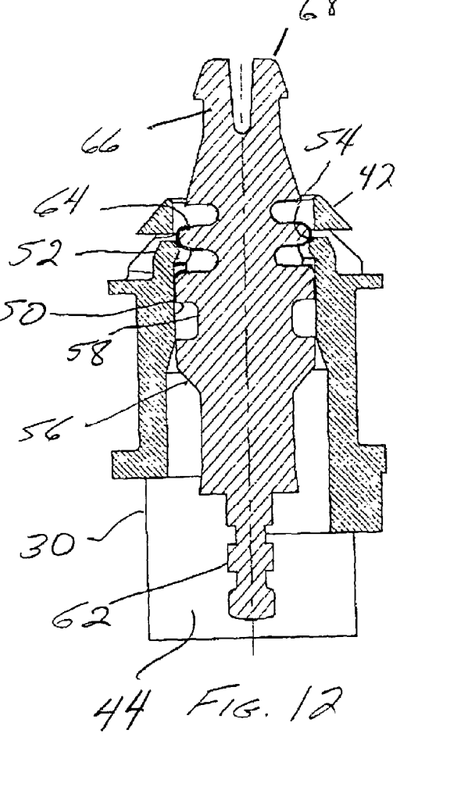
FIG. 12 is a cross-sectional view taken along line 12-12 of FIG. 11.
Figure 13:
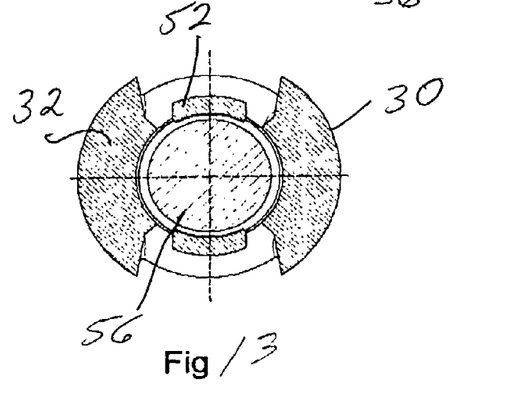
FIG. 13 is a cross-sectional view taken along line 13-13 of FIG. 11.

A mounting hole 50 extends longitudinally of the plunger assembly 30 through the seal end to the cavity 44. This hole 50 is best illustrated in FIG. 12. It is substantially circular in all transverse cross sections but for two detents 52 located diametrically opposed near the seal end 34 of the plunger assembly 30. The plunger body 32 is relieved around the detents 52 in order that they may have some resilience. As the relief is extended downwardly about the detents 52, greater resilience is realized. The detents 52 include an engagement surface 54 at an acute angle to the longitudinal direction of the plunger assembly 30. These engagement surfaces 54 extend inwardly into the otherwise generally cylindrical mounting hole 50.

A mandrel 56 is associated with the plunger assembly 30 in the mounting hole 50. This mandrel 56 includes an annular seal cavity 58 receiving an O-ring seal 60. The mounting hole 50 is relieved as best seen in FIG. 12 near the location of the O-ring seal 60 such that retraction of the mandrel 56 from the mounting hole 50 is facilitated. The inner end of the mandrel 56 includes an anchor pin 62 having a varied profile for bonding to a bungee molded in situ on the pin 62.

The mandrel 56 is relieved by annular grooves to define an annular flange 64. Further the mandrel 56 is preferably of a more resilient material than the body 32 of the plunger 30. This flexibility of the material along with the geometry of the annular flange 64 makes the flange 64 flexible longitudinally of the plunger. It extends radially outwardly and circumscribes the mandrel 56 at that location. The flange 64 is rounded at its periphery to a substantially semi-circular surface in cross section. This annular flange 64 is held against retraction of the mandrel 56 by the engagement surfaces 54 of the detents 52. This configuration offers more consistent extraction forces of the mandrel 56 from the mounting hole 50.

Resilient tines 66 are located at the outer end of the mandrel 56. These tines 66 are spaced apart and each includes a barb 68. The barbs 68 face outwardly away from one another and are defined by a segment of a truncated conical surface 70. The surfaces 70 each define a conical axis which extends longitudinally of the mandrel 56. These conical axes of the two surfaces 70 are offset from one another such that they approach one another as the resilient tines 66 are bent toward one another. In this way, the centers of the conical surfaces rather than their edges define the resistive force to insertion into the needle hub as discussed below.

The barrel 80 includes an open end 82 and a hub end 84. The hub end is illustrated in detail in various embodiments in FIGS. 14 through 20. The barrel includes a hub retainer 86 at the hub end 84. The body of the barrel 80 has an engagement flange 88 about the hub end 84 thereof. This engagement flange 88 receives shoulders 90 on the hub retainer 86 which has periodic longitudinal slits 92 to accommodate assembly. The retainer 86 includes a bore 94 therethrough coaxial with the barrel 80. Three dogs 96 extend into that bore 94 to retain a needle hub from moving inwardly into the barrel 80. The dogs 96 are resiliently mounted and have an inclined surface 98 to interact with the plunger assembly 30.

The needle hub 100 is located in the bore 94 of the barrel 80 at the hub end 84. The needle hub 100 includes a mounting body 102 and a lower engagement body 104. The mounting body 102 is generally cylindrical with a cavity to receive a needle 106. The needle 106 may be cemented in place.

The engagement body 104 includes an engagement hole 108 concentrically arranged at the inner end of the needle hub 100. This hole 108 is sized to receive the tines 66 of the mandrel 56, forcing the barbs inwardly. An engagement shoulder 110 receives the barbs once having passed through the hole 108. This secures the needle hub 100 to the mandrel 56. At the inner end of the engagement body 104, an inner surface 112 is provided for releasable retention by the dogs 96. An annular space is provided about the intersection between the mounting body 102 and the engagement body 104 and by the main body of the barrel 80 and the hub retainer 86 for an O-ring 114. The needle hub 100 is able to axially move a small amount within the hub retainer 86. This movement is resisted by the O-ring 114.

Figure 14:
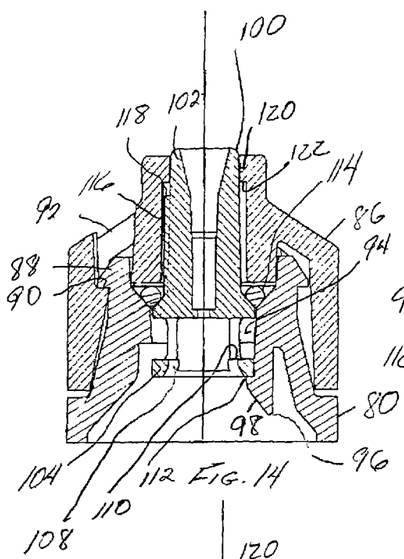
FIG. 14 is a cross-sectional detail of the forward end of the barrel taken along line 4-4 of FIG. 3.
Figure 15:
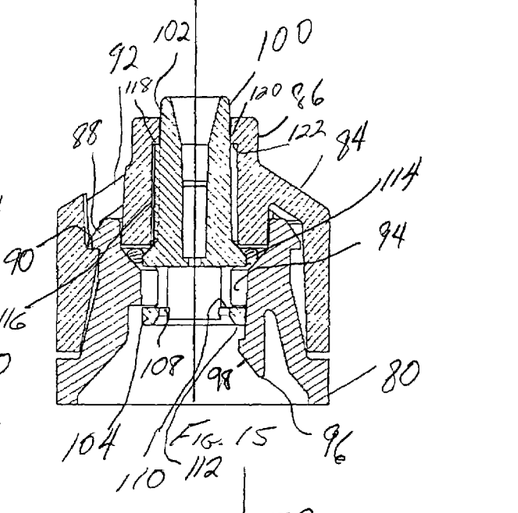
FIG. 15 is a cross-sectional view as in FIG. 14 with the needle hub advanced.

Having generally described the mounting of the needle hub 100 within the hub end 84 of the barrel 80, specific reference to the differences between embodiments are here addressed. FIGS. 14 and 15 constitute a first embodiment. In this embodiment, six longitudinally extending ribs 116 are located about the periphery of the mounting body 102. These ribs define a series of stops as a composite first shoulder 118. The hub retainer 86 includes an inwardly extending flange 120 having a second shoulder 122 which opposes the shoulder 118. These shoulders 118 and 122 are normal to the longitudinal direction of the barrel 80. Through a comparison of FIGS. 14 and 15, it can be seen that the needle hub 100 has a first position positioned against the dogs 96. A second position illustrated in FIG. 15 has the shoulders 118 and 122 engaged. These two positions are displaced from one another to a small extent. This spacing gives some additional advancement past the engagement of the mandrel 56 with the needle hub 100. The resistance of the O-ring 114 against movement of the needle hub 100 provides for engagement of the mandrel 56. However, further advance of the plunger assembly 30 may be needed to release the dogs 96. The operator will know to push harder until the needle hub 100 is released and the needle 106 retracts. Having the shoulders be normal to the longitudinal direcion of the barrel 80 defines a fixed second position. Without such a fixed limit to movement, the O-ring 114 can get hung up with the hub 100 or the components wedge together and inhibit needle retraction.

Figure 16:
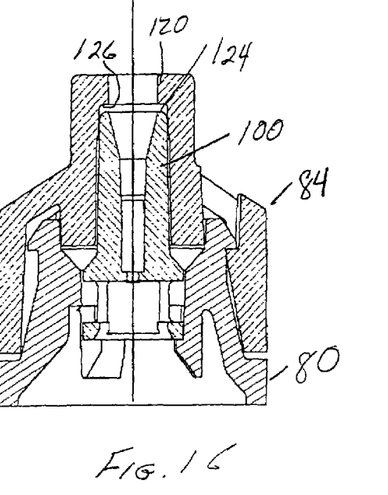
FIG. 16 is a cross-sectional view as in FIG. 14 of a second embodiment.
Figure 17:
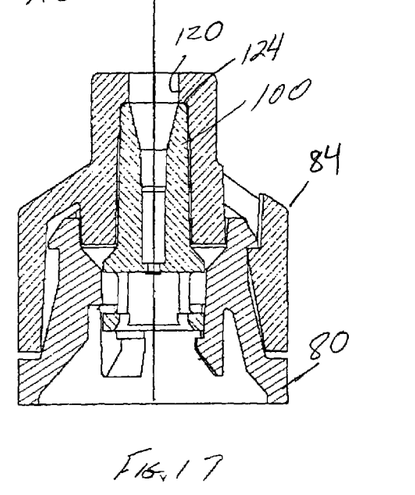
FIG. 17 is a cross-sectional view as in FIG. 15 of a second embodiment.
Figure 18:
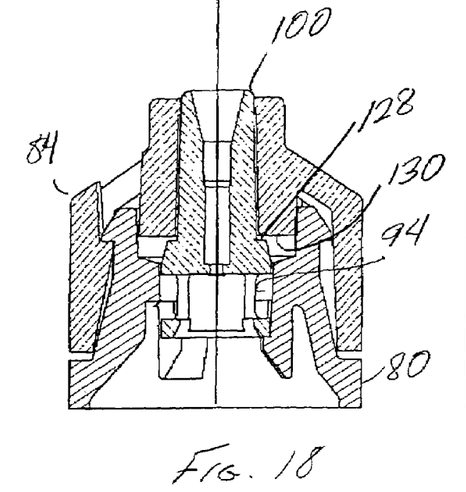
FIG. 18 is a cross-sectional view as in FIG. 14 of a third embodiment.
Figure 19:
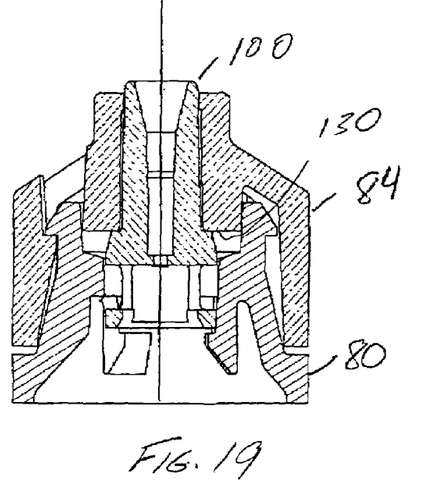
FIG. 19 is a cross-sectional view as in FIG. 15 of a third embodiment.
Figure 20:
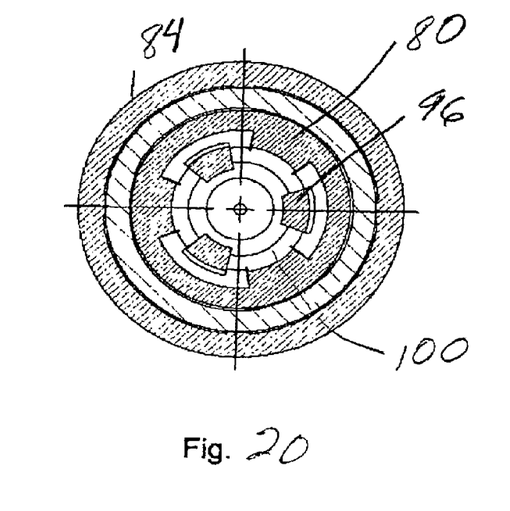
FIG. 20 is a cross-sectional view of any of FIGS. 14 through 19 looking forwardly in the barrel.

In FIGS. 16 and 17, another embodiment is employed where a first shoulder 124 is found at the outer end of the needle hub 100 and the flange 120 includes a second shoulder 126 receiving that shoulder 124. FIGS. 18 and 19 represent yet another embodiment where the first shoulder 128 is defined at the intersection between the mounting body 102 and the engagement body 104 while the resisting second shoulder 130 forms the lower end of the upper portion of the bore 94. A further embodiment is contemplated where an entire circular shelf is created at a location similar to that defined by the ribs 116 about the full periphery of the mounting body 102.

A spring element in the form of a bungee 140 is located within the cavity 44 of the plunger assembly. The bungee 140 is molded about the anchor pin 62 of the mandrel 56 at one end. At the other end, the bungee 140 is molded onto another anchor pin 142 of a catch 144. The catch 144 includes elements 146 which extend outwardly from the anchor pin 142. The barrel 80 includes an inwardly extending shoulder 148 which engages the elements 146 to prevent the catch from moving into the inner portion of the barrel 80.

The catch 144 also includes side elements 150 extending to a lesser extent outwardly from the anchor pin 142. These side elements 150 slide along the smooth surfaces 146 defining the cavity 44. There is some spring resilience to the plunger at the surfaces such that, in a relaxed position, the side elements 150 will be engaged by the two shoulders 48 and yet the catch 144 can move fairly easily within the cavity 44 toward the shoulders 48. This single set of shoulders 48 helps define a point at which the plunger assembly 30 is cocked the shoulders 48 can be positioned such that the thumb button can be grasped and the plunger easily retracted to charge the barrel 80. Likewise, the force profile in advancing the plunger assembly 30 provides clearer transition such that premature needle retraction can more easily be avoided.

Figure 4:
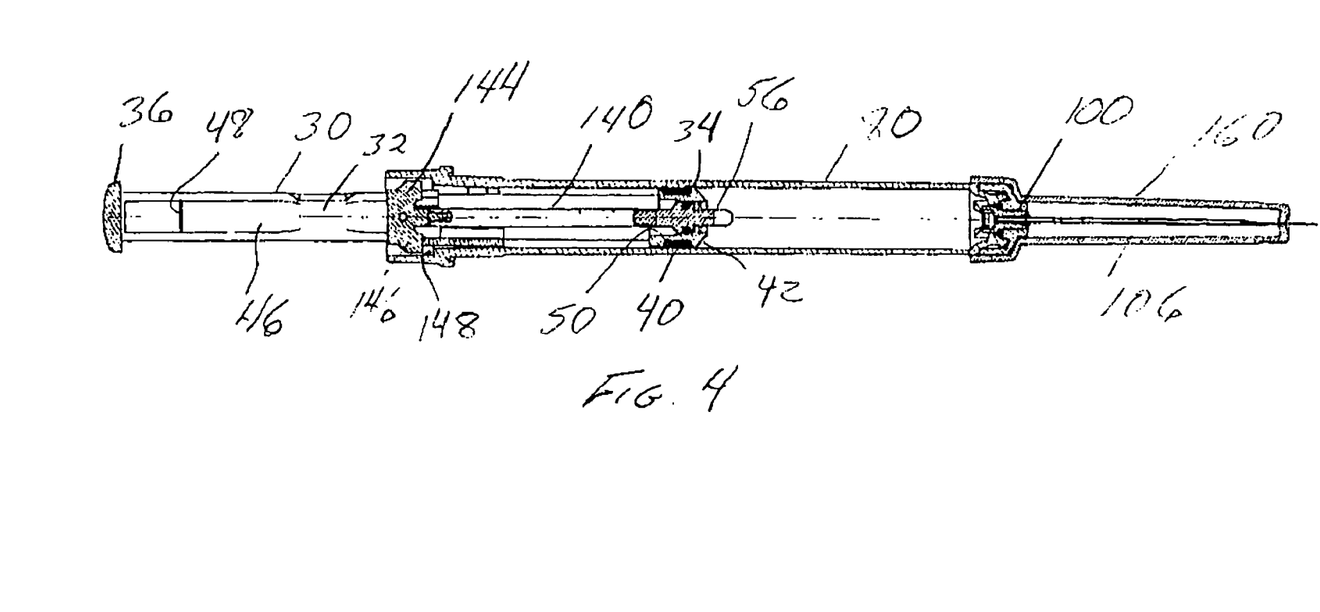
FIG. 4 is a cross-sectional view taken along line 4-4 of FIG. 3.

In operation, the syringe comes as illustrated in FIG. 1 with the plunger assembly 30 partially inserted into the barrel 80. A protective needle cap 160 isolates the needle 106. The configuration of FIG. 1 is also illustrated in FIG. 4. As can be seen, the bungee 140 can be in a relaxed or substantially relaxed condition to avoid any long term creep, thereby extending the shelf life of the syringe.

Figure 5:
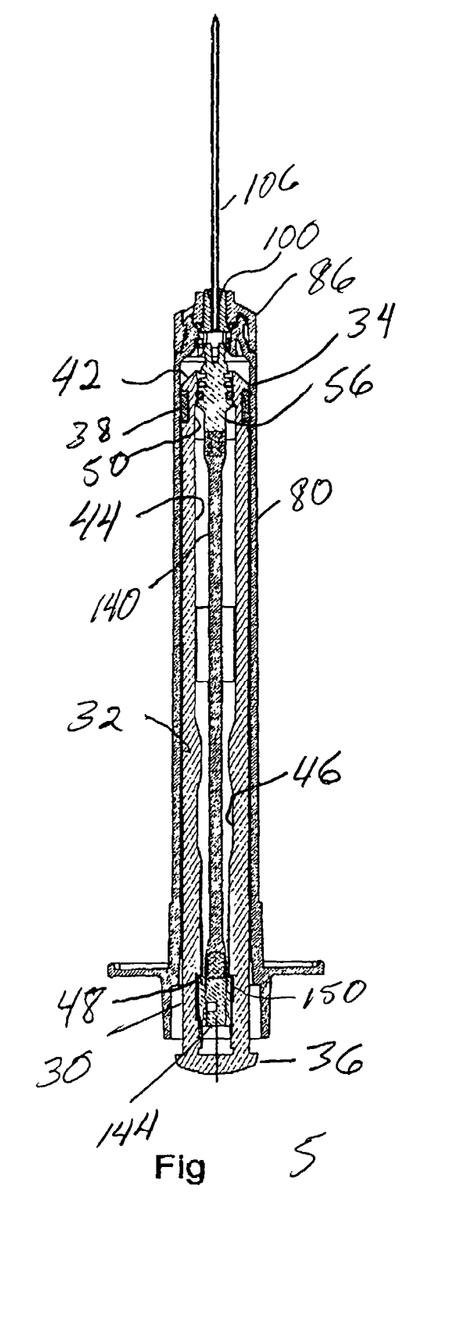
FIG. 5 is a cross-sectional view as in FIG. 4 with the plunger moved.
Figure 6:
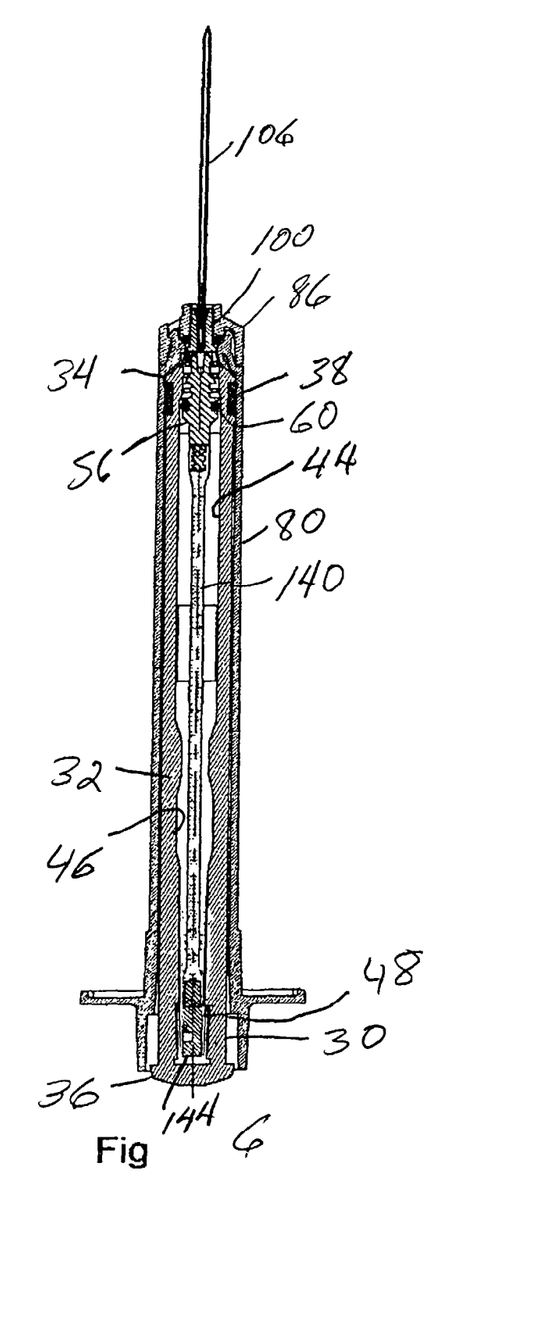
FIG. 6 is a cross-sectional view as in FIG. 4 with the plunger moved.
Figure 7:
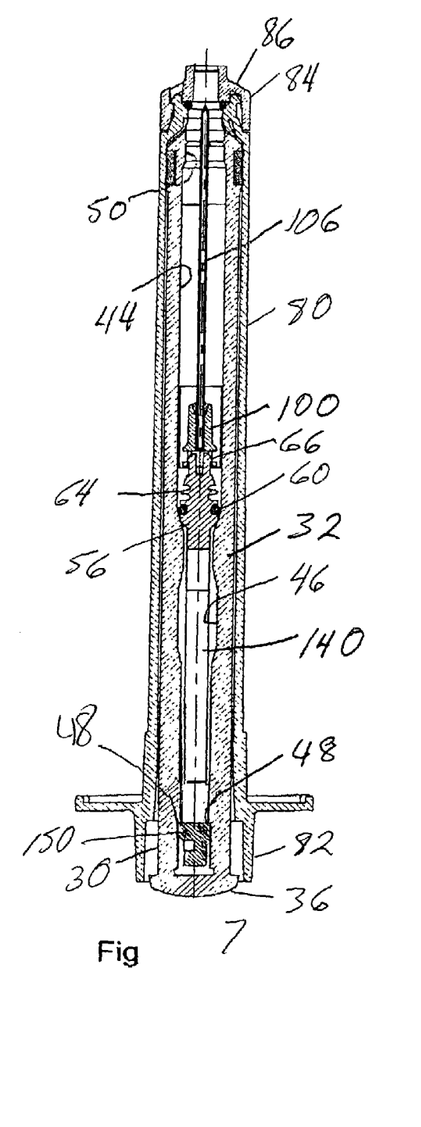
FIG. 7 is a cross-sectional view as in FIG. 4 with the needle retracted. 4.
Figure 7A:
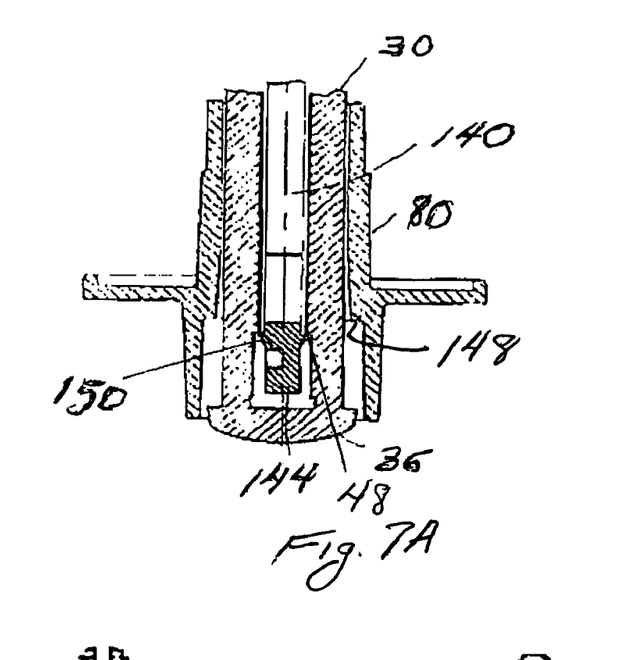
FIG. 7A is a cross-sectional detail as seen in FIG. 4.
Figure 7B:
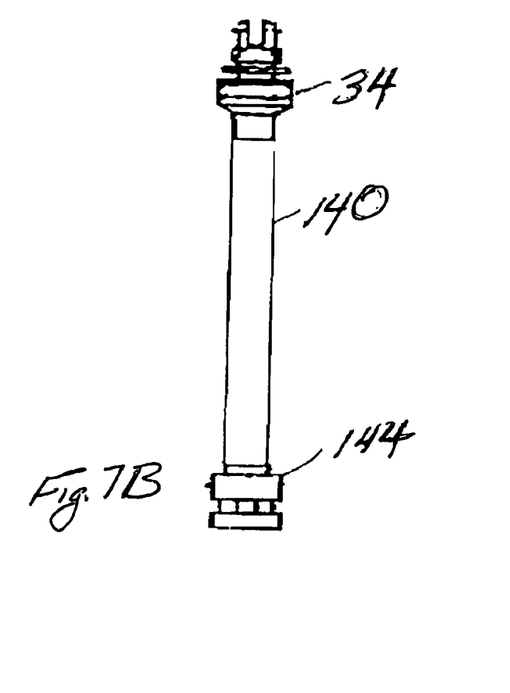
FIG. 7B is a front view of a bungee with a mandrel and a catch.
Figure 7C:
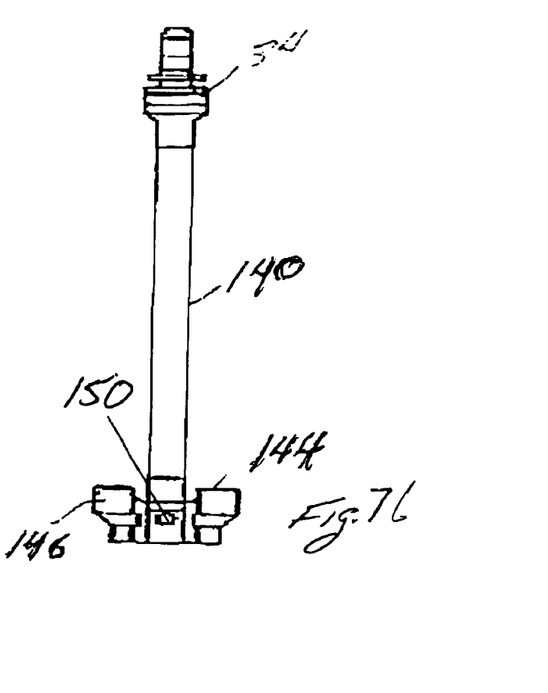
FIG. 7C is a side view of the assembly of FIG. 7B.
Figures 8, 9:
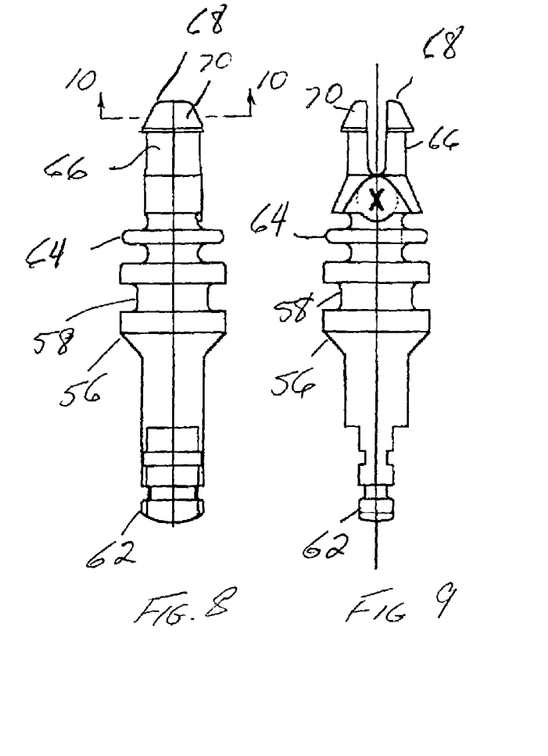
FIG. 8 is a side view of a mandrel.
FIG. 9 is a front view of a mandrel.
Figure 10:
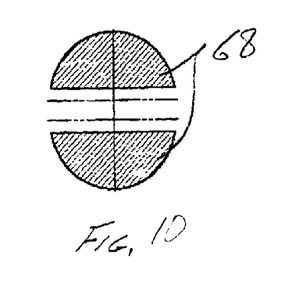
FIG. 10 is a cross-sectional view taken along line 10-10 of FIG. 8.

FIG. 5 illustrates an advance of the plunger 30 substantially fully into the barrel 80. As the catch 144 is prevented from entering the barrel because of the elements 146 engaging the shoulder 148, the bungee 140 is stretched and tensioned by this insertion. Further, the catch 144 comes into engagement with the shoulder 148 on the smooth surfaces 46 of the cavity 44.

With the shoulders 148 engaging the catch 144, the bungee will remain in tension until such time as the mandrel 56 is extracted from the mounting hole 50. The bungee will not lose tension as the plunger assembly 30 is drawn back to intake the substance to be injected.

Once the appropriate amount of fluid is drawn into the syringe, the injection may be given until the plunger assembly 30 again is fully within the barrel 80. The syringe may then be withdrawn from the injection site and further pressure exerted against the thumb button of the outer end 36 of the plunger assembly 30. This action drives the resilient tines 66 into the engagement hole 108 of the needle hub 100 to the point that the barbs 68 engage the engagement shoulder 110 within the engagement body 104. Concurrently, the driver surface 42 on the seal end 34 of the plunger assembly 30 engages the inclined surfaces 98 of the dogs 96 and forces them outwardly to release the needle hub 100. The engagement of the needle hub 100 with the mandrel 56 requires less force than and precedes the release of the mandrel 56 from the mounting hub 50.

With the dogs 96 retracted and the mandrel 56 engaged with the needle hub 100, the mandrel 56 is released from the seal end 34 of the plunger assembly 30 and tensioned bungee retracts the needle hub 100 and the needle 106 into the cavity 44 of the plunger assembly 30. This last condition can best be seen in FIG. 7. In the retraction, the annular flange 64 is flexed longitudinally by being dished toward the outer end of the mandrel 56. This releases the mandrel 56 from the detents 52 to permit retraction of the bungee 140 and withdrawal of the mandrel 56. Once the mandrel has been separated from the mounting hole 50, the assembly cannot be reused as a syringe without full disassembly of the device.

Accordingly, an improved syringe having a retractable needle is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A hypodermic syringe comprising
a barrel including an open end and a hub end having a hub retainer;
a plunger including a seal end slidably disposed in the barrel, an outer end extending from the open end of the barrel, a cavity between the outer end and the seal end, a mounting hole extending longitudinally of the plunger through the seal end to the cavity and a driver surface on the seal end;
a mandrel in the mounting hole;
a spring element in the cavity fixed to the mandrel at a first end and fixable relative to the plunger in tension at a second end;
a needle hub in the hub retainer, the hub end of the barrel including resiliently mounted dogs releaseably retaining the needle hub from movement longitudinally into the barrel and engageable with the driver surface to release the needle hub for movement longitudinally into the barrel, the hub retainer having a bore and a first shoulder in the bore facing the plunger and being normal to the longitudinal direction of the barrel, the needle hub including longitudinally extending ribs about the needle hub defining a second shoulder on the ends thereof facing the first shoulder and being normal to the longitudinal direction of the barrel, a first position with the needle hub against the dogs, a second position with the second shoulder against the first shoulder, the first and second positions being displaced from one another.

2. The hypodermic syringe of claim 1 further comprising an O-ring, the needle hub further including an outwardly extending flange, the O-ring being between the flange and the hub retainer resiliently resisting movement of the needle hub from the first position.

3. A hypodermic syringe comprising a barrel including an open end and a hub end;

a plunger including a seal end slidably disposed in the barrel, an outer end extending from the open end of the barrel, a cavity between the outer end and the seal end and a mounting hole extending longitudinally of the plunger through the seal end to the cavity, the cavity including two opposed smooth walls with one shoulder only in each wall facing the outer end and aligned with one another;

a mandrel in the mounting hole;

a spring element in the cavity fixed to the mandrel at a first end;

a catch slideably mounted in the cavity and fixed to the spring element at a second end, the catch including first elements engageable with the barrel and second elements engageable with the shoulders, the second elements beinci engageable with the shoulders restricting movement toward the seal end and slidable past the shoulders toward the outer end.

* * * * *